United States Patent [19]

Ronchetti et al.

[11] 4,426,618
[45] Jan. 17, 1984

[54] PROBE FOR THE CONTINUOUS IN-SITU MEASUREMENT OF THE CORROSION RATE OF PIPES AT HIGH TEMPERATURE OR HAVING HIGH-RESISTIVITY LIQUIDS FLOWING THERETHROUGH

[75] Inventors: Camillo Ronchetti, Milan; Pierantonio Borroni, Bussero; Giovanni Buzzanca, Bergamo, all of Italy

[73] Assignee: C.I.S.E. SpA, Italy

[21] Appl. No.: 315,391

[22] Filed: Oct. 27, 1981

[30] Foreign Application Priority Data

Nov. 4, 1980 [IT] Italy ............................... 25758 A/80

[51] Int. Cl.³ .......................................... G01R 27/02
[52] U.S. Cl. .................................................. 324/65 CR
[58] Field of Search ................. 324/65 CR, 65 P, 61 P

[56] References Cited

U.S. PATENT DOCUMENTS 3,418,848 12/1968 Schaschl .................... 324/65 CR

Primary Examiner—Stanley T. Krawczewicz
Assistant Examiner—Jose M. Solis
Attorney, Agent, or Firm—Karl W. Flocks; Sheridan Neimark; A. Fred Starobin

[57] ABSTRACT

The invention relates to a probe for the continuous in-situ measurement of the rate of corrosion of pipes subjected to high temperatures or having highly resistive fluids flowing therethrough, by a measurement of the polarization resistance, characterized in that it comprises: electrodes of tubular form one of which is the working electrode, adapted to provide an extension of a pipeline, said electrodes being alternately spaced apart with dielectric spacers, means for connecting said electrodes to said pipeline between two sections of the pipeline, and resilient or nearly resilient gaskets to provide sealtightness between said electrodes, spacers, connectors and pipe sections.

4 Claims, 1 Drawing Figure

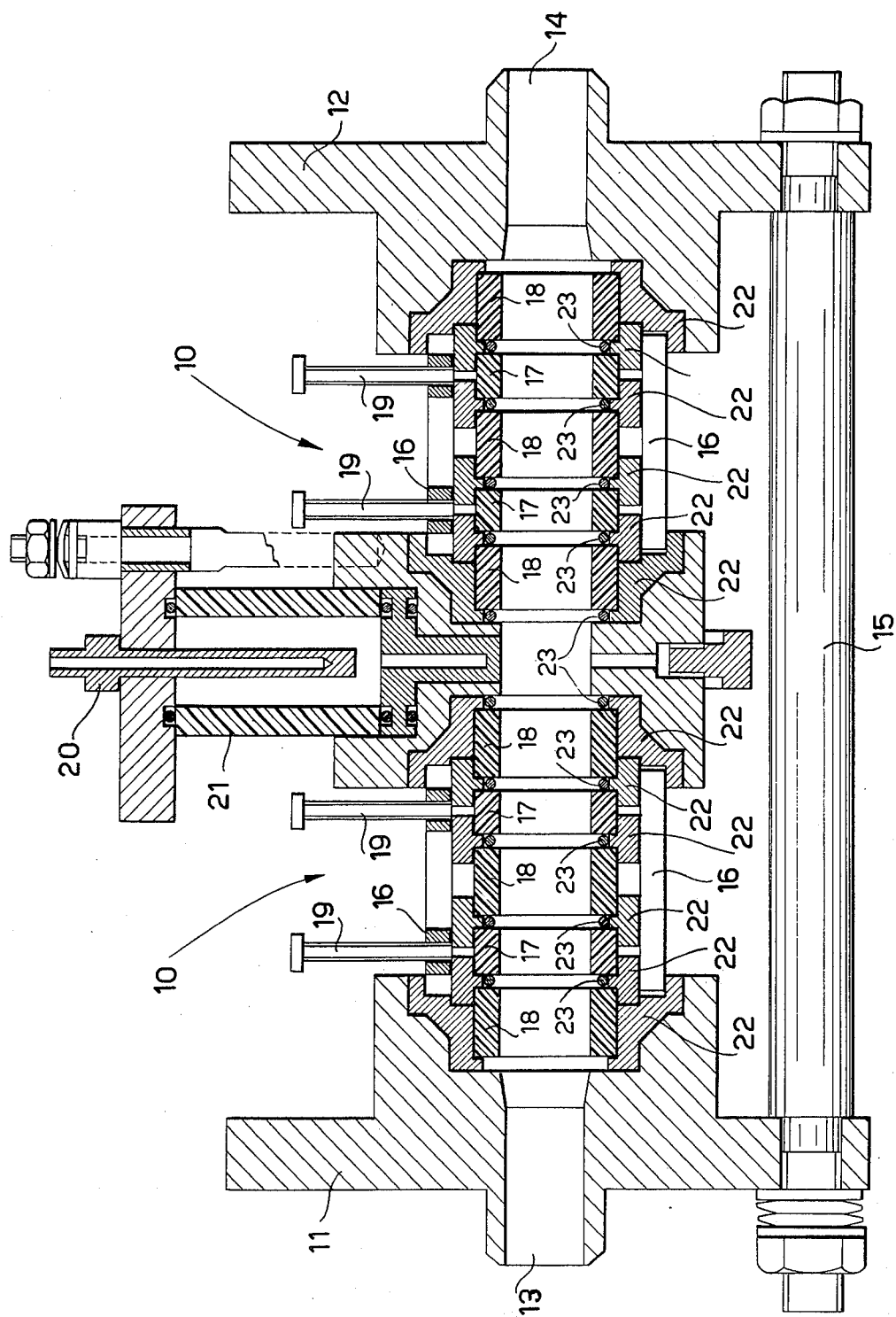

PROBE FOR THE CONTINUOUS IN-SITU MEASUREMENT OF THE CORROSION RATE OF PIPES AT HIGH TEMPERATURE OR HAVING HIGH-RESISTIVITY LIQUIDS FLOWING THERETHROUGH

When determining the corrosion of metallic materials, it is customary to carry out, in the majority of the cases, weight measurements: these latter, however, have certain limitations, that is, the values integrate the phenomenon along longer or shorter times, during which the rate of corrosion is not constant. The duration of the tests is subordinate to the obtention of significant weight differentials. The result possibly integrates also those weight variations which take place at the start or the end of the test, when the chemical conditions are not those under test (circuit start transients and the like) and the measurement of the instantaneous rate is impossible especially during the transitional states, and it is necessary to know the behaviour of the insoluble products of the corrosion (formation of partially or totally sticking deposits and so on).

These limitations are particularly evident in the case of carbon steels or low-alloyed steels, since it is necessary to determine the rate of corrosion during the starts, the times of formation of the protective oxide films (passivation), the resistance of said films as the chemical conditions worsen and the values of the rate of corrosion under equilibrium conditions.

It is thus an asset to be able to determine the instantaneous rate of corrosion by measuring the polarization resistance.

A few authors have carried out test in high purity water on carbon steels in static autoclaves: B. E. Wilde, The Influence of Hydrogen, Oxygen, and Ammonia on the Corrosion Behaviour of Plain Carbon Steels in High Temperature Water, Corrosion, Vol. 24, No 10, (1968) and with rotary electrodes, at room temperature: Z. A. Foroulis, "The Effect of Oxygen on the Corrosion of Iron in High Purity Water", Proceedings of the Fifth International Congress of Metallic Corrosion, Tokyo, Japan, May 1972, and have emphasized the advantages and the difficulties of this technology. As a matter of fact it is required, in order that valid results may be obtained for the actual installations, that measurement electrodes be used, which reproduce the true thermal and hydraulic conditions.

In this connection, it is appropriate to set forth a few preliminary considerations of a theoretical nature.

When a corrodible electrode is polarized in a DC circuit, the Stern and Geary formula is valid between the overvoltage, $\eta$, and the density of the applied current, i:

$$i = 2.3 \, i_{corrosion} \, \eta \, \frac{-\beta c + \beta a}{\beta c \cdot \beta a} \qquad (1)$$

or, also:

$$i_{corrosion} = \frac{\beta c \cdot \beta a}{2.3(\beta c + \beta a)} \cdot \frac{i}{\eta} \qquad (2)$$

wherein $\beta_c$ and $\beta_a$ are the cathodic and the anodic slope, respectively, of the Tafel's straight lines for the metal in the corrosive means concerned, $i_{corrosion}$ is the instantaneous rate of corrosion $\eta$ is the overvoltage, defined in terms of difference between the corrosion potential $E_{corrosion}$ and the electrode potential as measured at the current density i.

It has been ascertained by field tests that the relationship between $\eta$ and i is linear within an interval of about 10 mV.

The slope of the straight line in question, within that range, is called the polarization resistance ($R_p$) because, under the electric experimental conditions, it behaves like a conventional electric resistor, that is:

$$\frac{\eta}{i} = R_p \qquad (3)$$

Inasmuch as the term $\beta c. \, \beta a/2.3.(\beta c + \beta a)$ is a constant for a given corrosion system, that is $$\frac{\beta c \cdot \beta a}{2.3 \cdot (\beta c + \beta a)} = k \qquad (4)$$

now, therefore, the equation (2) can be written in this way:

$$i_{corrosion} = k \cdot \frac{1}{R_p} \qquad (5)$$

Furthermore, the corrosion rate ($i_{corrosion}$) is expressed, rather than in terms of current density ($\mu A.cm^{-2}$), in terms of weight loss per unit of surface and of time, that is, $\bar{r}(mdd)$, so that $$\bar{r} = k' \cdot \frac{1}{R_p} \qquad (6)$$

In order that the maximum accuracy may be obtained in the measurements, it is vital that the determination of the overvoltage $\eta$ be free from any error.

As a rule, $\eta$ sums up the contribution of three terms, viz.:

activation overvoltage $\eta_a$
concentration overvoltage, $\eta_c$, and
resistive overvoltage, $\eta_R$, called also IR drop.

To the ends of the accuracy of the measurements, the only term of interest is $\eta_a$. Under the most favourable test conditions, the terms $\eta_c$ and $\eta_R$ can be made virtually nil (6,7). For example, in stirred solutions having a comparatively low resistivity.

In the case in which high-resistivity solutions are used, which is of specific interest in the case in point, a few precautions could be taken to dispose of both $\eta_c$ and $\eta_R$. The polarization current can be selected small enough as to virtually dispose of $\eta_c$, but significant errors due to $\eta_R$ can be found even when using the well known Haber-Luggins probe.

The origin of such errors is connected to the resistance of the corrosive means ($R\Omega$) comprised between the working electrode and the probe, even when the probe tip is very close.

The difficulty inherent in the necessity of measuring values of $R_p$ exempt from the resistive term $R\Omega$ has severely limited the works concerning the corrosion rate in high purity water. In this connection reference is invited to the papers by Wilde on the corrosion of iron in high-temperature autoclaves, in which the Author provides to correct the measured overvoltage of the resistive drop by means of an electric bridge circuit (B. E. Wilde "Adaptation of Linear Polarization Techniques for In-Situ Corrosion Measurements in Water- Cooled Nuclear Reactor Environments", Corrosion, December 1967, page 379.

SUMMARY OF THE INVENTION

An object of the present invention is to suggest a device for the measurement of corrosion in installations having pipelines through which highly resistive fluids flow, more particularly high temperature pipelines, wherein the characteristics and the layout of the installation allow, as far as possible, to reproduce the actual corrosion conditions in such pipelines while concurrently circumventing the problems connected with the measurement devices suggested by the prior art as outlined above.

To achieve these objects, the present invention suggests a probe for the continuous in-situ measurement of the rate of corrosion in pipes subjected to high temperatures or having highly resistive liquids flowing therethrough, by a measurement of the polarization resistance, characterized in that it comprises electrodes of a tubular shape, either of which is the working electrode, adapted to make up the extension of a pipeline, said electrodes being alternately spaced apart with dielectric spacers and with resilient and nearly resilient sealing gaskets, and means for connecting said electrodes to said pipeline between two sections thereof.

In order that the characteristics and the advantages of the invention may be best understood, an exemplary embodiment will now be described hereinafter, without any limitation, reference being had to the FIGURE of the accompanying drawing.

BRIEF DESCRIPTION OF THE DRAWINGS

The sole FIGURE in the drawings shows the probe cross-section.

DESCRIPTION OF THE PREFERRED EMBODIMENT

The FIGURE shows a diametrical cross-sectional view of a couple of probes according to the invention, indicated at 10, which are adapted to be used in an installation having pipelines subjected at high temperatures. The two probes are operatively connected to one another serially, so as to do away with possible electric disturbances and thus to offset any influence thereof on the measurement readings.

For connecting the probes 10 to the pipes of the installation, terminal headers 11 and 12 are provided, to be affixed to the pipes, and having a central opening at 13 and 14 to receive the two sections of a pipeline of the installation.

The terminal headers aforesaid are mutually connected by a pitman 15 for sealing in the operative stage of the pipeline-probe assembly.

Each of said two probes 10 comprises a hollow cylindrical casing 16 which houses two tubular electrodes, 17, that is to say, a working electrode and a counter-electrode, formed from the sections of the same pipe connected to the probe.

To provide electrical insulation therebetween, the two electrodes are interspaced with spacers 18, also tubular in shape, made of a stiff dielectric material.

The casing 16 has a couple of seats for the electric contacts 19 which connect the couple of the electrodes 17 to a corrosion meter.

In a position intermediate between the two probes 10 a reference electrode 20 is connected to measure the voltages, and it is electrically insulated by spaces 21 made of a stiff dielectric material.

To provide a tight seal between the several pieces which compose the probe, and also between the probe as such and the headers for securing the probes to the pipes, a gasket system is provided which consists of a set of O-rings 23 made of a resilient material, and a set of gaskets 22 of a nearly resilient dielectric material.

As can be seen in the foregoing disclosure, according to the invention, the couple of electrodes which give the required measurements are preferably made with sections having the same dimensions of the installation being tested and, virtually, they are an extension of the pipelines thereof. By measuring the polarization resistance, the probe is thus in a position to give real and accurate responses about the conditions of corrosion of the pipelines concerned.

However, the practical working of such a basic idea, according to which the measuring probe is directly connected to pipings having a fluid flowing therethrough, could not dispense with the sealing problems existing between the several component parts, such problems being considerably aggravated by the fact that the pipelines were subjected to high temperatures and were under pressure.

As a matter of fact, the pieces which compose the probe are subjected to continuous heat shocks which are added to the mechanical and hydraulic thrusts due to the flow of the liquid in the interior of the pipeprobe assembly.

The solution of this secondary problem is given, according to the invention, by the assembly of nearly resilient gaskets, since field tests have shown that such an assembly is capable of providing a twofold softening action between the stiff component parts of the system, such as the electrodes, the casing and the spacers of the probe, and the probe itself with its sealing ends: concurrently, the pushes due to heat shocks and fluid pressure in the system, which are more pronounced under conditions of high temperature as used in the application field of the invention, are efficiently counteracted.

The probe according to this invention, in the preferred application envisaged therefor, is directly connected to the two pipe sections in which it is desired to know the magnitude of the corrosion phenomena and, to this purpose, the probe is designed each time consistently with the different specific applications.

When, however, the pipes have so high a diameter as to give rise to serious problems as to jointing and sealing for the probe, the invention provides so that the probe is connected, rather than directly to the pipes to be tested, to a by-pass piping having reduced dimensions, thereby providing a higher degree of safety for the system.

It is understood that the arrangement of the electrodes in the probe of this invention, as well as the structure of the third electrode, may be embodied by a number of alternative arrangements without thereby departing from the scope of the invention.

For example, a tubular configuration may be imparted also to the reference electrode, so that the result is an arrangement with three symmetrical tubular electrodes: a counter-electrode may be mounted axially in the probe, or, as another alternative, a free central electrode, that is a non-polarized electrode, may also be provided.

In both the last named two approaches, the presence of the central conductor provides an even distribution of the current density on the working electrode.

We claim:

1. A probe for the continuous in-situ measurement of the corrosion rate of pipes subjected to high temperatures or having highly-resistive fluids flowing therethrough, by measuring the polarization resistance comprising a section of pipe, means to mount said section of pipe at the ends and in a path receiving therethrough at least some of the flow of the pipes whose measurement of corrosion rate is being made, said section of pipe including a couple of electrodes of a tubular shape, one of which is the working electrode, dielectric spacers alternately spacing apart said electrodes, and resilient and nearly resilient gaskets to provide a tight seal between said electrodes, spacers, mounting means, and pipes.

2. Probe according to claim 1, characterized in that it comprises at least an axially arranged electrode.

3. Probe according to claim 2, characterized in that said axially arranged electrode is the counter electrode.

4. Probe according to claim 2, characterized in that said axially arranged electrode is a free conductor.

* * * * *